United States Patent
Wang et al.

(10) Patent No.: US 10,023,859 B2
(45) Date of Patent: *Jul. 17, 2018

(54) FABRICATION OF HIERARCHICAL SILICA NANOMEMBRANES AND USES THEREOF FOR SOLID PHASE EXTRACTION OF NUCLEIC ACIDS

(71) Applicant: THE JOHNS HOPKINS UNIVERSITY, Baltimore, MD (US)

(72) Inventors: Tza-Huei Wang, Timonium, MD (US); Yi Zhang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 17 days.

This patent is subject to a terminal disclaimer.

(21) Appl. No.: 15/382,807

(22) Filed: Dec. 19, 2016

(65) Prior Publication Data

US 2017/0096660 A1    Apr. 6, 2017

Related U.S. Application Data

(62) Division of application No. 14/341,957, filed on Jul. 28, 2014, now Pat. No. 9,765,325.

(60) Provisional application No. 61/862,319, filed on Aug. 5, 2013.

(51) Int. Cl.

| | |
|---|---|
| *C12Q 1/6806* | (2018.01) |
| *C12N 15/10* | (2006.01) |
| *C25D 1/00* | (2006.01) |
| *B01D 71/02* | (2006.01) |
| *B01D 67/00* | (2006.01) |
| *B01J 20/10* | (2006.01) |
| *B01J 20/26* | (2006.01) |
| *B01J 20/28* | (2006.01) |
| *B01J 20/32* | (2006.01) |
| *C23C 14/10* | (2006.01) |
| *C23C 14/22* | (2006.01) |
| *C23C 16/44* | (2006.01) |
| *C25D 13/02* | (2006.01) |
| *C25D 13/12* | (2006.01) |
| *C23C 18/12* | (2006.01) |
| *B01D 69/06* | (2006.01) |

(52) U.S. Cl.
CPC ..... *C12N 15/1006* (2013.01); *B01D 67/0069* (2013.01); *B01D 67/0072* (2013.01); *B01D 67/0083* (2013.01); *B01D 71/027* (2013.01); *B01J 20/103* (2013.01); *B01J 20/261* (2013.01); *B01J 20/28035* (2013.01); *B01J 20/321* (2013.01); *B01J 20/3225* (2013.01); *B01J 20/3234* (2013.01); *B01J 20/3297* (2013.01); *C12Q 1/6806* (2013.01); *C23C 14/10* (2013.01); *C23C 14/221* (2013.01); *C23C 16/44* (2013.01); *C25D 1/006* (2013.01); *B01D 69/06* (2013.01); *C23C 18/1212* (2013.01); *C25D 13/02* (2013.01); *C25D 13/12* (2013.01)

(58) Field of Classification Search
CPC .... C12N 15/1006; C12Q 1/68; C23C 14/221; B01D 67/0083
See application file for complete search history.

(56) References Cited

U.S. PATENT DOCUMENTS

| | | |
|---|---|---|
| 2005/0106602 A1 | 5/2005 | Akhavan-Tafti |
| 2005/0112650 A1 | 5/2005 | Chang et al. |
| 2013/0052721 A1 | 2/2013 | Hollander et al. |
| 2013/0164819 A1 | 6/2013 | Sjoblom et al. |

FOREIGN PATENT DOCUMENTS

| | | |
|---|---|---|
| WO | 2010/027283 A1 | 3/2010 |
| WO | 2010/132610 A2 | 11/2010 |

OTHER PUBLICATIONS

Zhang, Y., et al., "Spontaneous shrinking silica nanomembrane for solid phase DNA extraction", IEEE Nano/Micro Engineered and Molecular Systems, 8th Annual Conference, Suzhou China: IEEE Apr. 7-10, 2013, p. 29, Article No. 243 (1E1-3).
International Search Report dated Nov. 21, 2014 for application PCT/US2014/048352.

*Primary Examiner* — Narayan Bhat
(74) *Attorney, Agent, or Firm* — John Hopkins Technology Ventures

(57) ABSTRACT

The present invention provides a novel method to fabricate silica nanostructures on thin polymer films based on silica deposition and self-wrinkling induced by thermal shrinkage. These micro- and nano-scale structures have vastly enlarged the specific area of silica, thus the silica nanomembranes can be used for solid phase extraction of nucleic acids. The inventive silica nanomembranes are suitable for nucleic acid purification and isolation and demonstrated better performance than commercial particles in terms of DNA recovery yield and integrity. In addition, the silica nanomembranes have extremely high nucleic acid capacity due to its significantly enlarged specific surface area of silica. Methods of use and devices comprising the silica nanomembranes are also provided.

19 Claims, 8 Drawing Sheets

FABRICATION OF HIERARCHICAL SILICA NANOMEMBRANES AND USES THEREOF FOR SOLID PHASE EXTRACTION OF NUCLEIC ACIDS

REFERENCE TO RELATED APPLICATIONS

This application is a Divisional application of U.S. patent application Ser. No. 14/341,957, filed Jul. 28, 2014, which claims the benefit of U.S. Provisional Patent Application No. 61/862,319, filed on Aug. 5, 2013, both of which are hereby incorporated by reference for all purposes as if fully set forth herein.

STATEMENT OF GOVERNMENTAL INTEREST

This invention was made with government support under grant numbers CA155305 and CA151838 awarded by the National Institutes of Health. The government has certain rights in the invention.

BACKGROUND OF THE INVENTION

A fundamental problem in nucleic acid analysis is sample preparation. The sample to be investigated usually comprises cells or tissue with interfering, partially insoluble constituents (known as debris) which can interfere with the subsequent isolation and analysis. Such insoluble constituents occur particularly in the case of nucleic acid isolation from stool/feces, blood, warts, calcified structures (bones), or else heavily necrotic tissue samples. However, debris can, in the broadest sense, also include soluble components, for example released hemoglobin from erythrocytes which is present in a great excess and will be removed during the isolation of the nucleic acids.

Isolation of nucleic acids from samples such as cells, tissues, plants, bacteria, viral particles, blood, serum, or plasma, is a critical step for downstream genetic analysis. Conventionally, liquid phase extraction techniques, such as phenol/chloroform precipitation, are widely used. Although these approaches yield nucleic acids of high quality, they are laborious, time-consuming and highly operator-dependent. Solid phase extraction techniques are a popular alternative. They are often the methods of choice when processing large numbers of samples. Commonly used solid-phase substrates include silica spin columns and silica magnetic particles that provide large surface areas for nucleic acid binding. However these porous matrices and micro/nano particles induce DNA shearing as a result of flow and particle mixing, leading to decreased DNA integrity.

Molecular analysis of Formalin Fixed Paraffin Embedded (FFPE) samples represents another area where advances in sample preparation are needed. Despite the growing need for and the demonstrated potential advantages of molecular biomarkers, it has proven difficult to routinely employ them in the diagnosis and management of patients. One reason for this failure has been the logistical challenges of obtaining, rapidly processing, storing, and transporting quick-frozen tissue samples in clinical settings. Standard hospital tissue processing involves fixation in formaldehyde, followed by embedding in paraffin blocks, then by subsequent sectioning and staining of these blocks to generate FFPE samples.

If these FFPE samples could be harnessed for molecular analysis, the potential for revolutionizing current medical practice exists. FFPE blocks obtained in hospital pathology departments could then be routinely assayed using the newer molecular methods, in addition to standard morphological and histological analysis. Moreover, since FFPE samples are usually stored for many years by hospital pathology departments, retrospective molecular evaluations could also be performed, empowering researchers to conduct molecular epidemiologic studies on large cohorts with known clinical outcomes. New technologies are needed such that molecular pathologic assays could be devised or adapted to work on these FFPE samples.

However, as FFPE preservation was originally designed to stabilize morphological and histological features rather than preserve molecular information, the DNA/RNA contained within are often fragmented due to the FFPE preservation process, due to oxidation, and due to poor storage conditions (i.e. long-term archival at room temperature). In addition, FFPE tissues contain contaminating formalin and paraffin wax as well as heavily cross-linked DNA/RNA that can inhibit downstream assays.

As such, there exists an unmet need to develop novel separation materials and methods which allow for easier isolation and purification of nucleic acids from a clinical sample, including FFPE samples.

SUMMARY OF THE INVENTION

The present inventors have developed a new DNA/RNA extraction method based on novel and inexpensively fabricated hierarchical silica nanomembranes, which have been named "Nanobind." Nanobind is a polymer substrate containing a hierarchical topography of microscale wrinkles and nanoscale silica flakes. Unlike beads and columns which impart DNA/RNA fragmenting shear forces, the non-porous Nanobind substrate can bind and release DNA/RNA without fragmenting it, achieving DNA/RNA integrity (>48 kbp) which matches gold standard phenol-chloroform extractions with a process that is simpler than beads and columns (e.g. no magnets, high speed centrifugation, or tube transfers). Furthermore, Nanobind has a binding capacity that is at least 5-30 fold greater than known methods employing beads and/or columns. It is known that using increased starting material in assays can offset the deleterious effects of damaged FFPE DNA/RNA. Thus, the ability of Nanobind to achieve high DNA integrity combined with its higher extraction efficiency and its ability to load significantly more tissue into a single extraction can greatly increase molecular assay sensitivity and reproducibility (i.e. more DNA/RNA of higher quality).

In accordance with an embodiment, the present invention provides a silica nanomembrane comprising a heat shrunken polymer core and coated with a silicon dioxide layer, wherein the silicon dioxide layer comprises a plurality of microscale wrinkles and nanoscale silica flakes.

In accordance with another embodiment, the present invention provides a method for making a silica nanomembrane comprising: a) depositing onto a polymer film or core having an original size, a layer of silicon dioxide; and b) heating the composition of a) at a sufficient temperature and time to allow the polymer film or core to shrink, and wherein the shrinking of the polymer film or core creates silica microstructures and/or nanostructures on the surface of the layer of silica on the silica nanomembrane.

In accordance with a further embodiment, the present invention provides a method for extracting nucleic acids from a sample comprising: a) obtaining a sample comprising nucleic acids; b) contacting the sample with a sufficient amount of silica nanomembranes; c) allowing the nucleic acids in the sample to adsorb onto the silica nanomembranes; d) washing the silica nanomembranes to remove any non-nucleic acid components; and e) desorbing the nucleic acids from the silica nanomembranes to obtain the isolated and purified nucleic acids from the sample.

In accordance with an embodiment, the present invention provides A method for extracting nucleic acids from formalin fixed paraffin embedded (FFPE) samples comprising:

a) obtaining a FFPE sample comprising nucleic acids; b) deparaffinizing the sample; c) contacting the sample with a sufficient amount of silica nanomembranes; d) allowing the nucleic acids in the sample to adsorb onto the silica nanomembranes; e) washing the silica nanomembranes to remove any non-nucleic acid components; and f) desorbing the nucleic acids from the silica nanomembranes to obtain the isolated and purified nucleic acids from the sample.

In accordance with an embodiment, the present invention provides a device for extracting nucleic acids from a sample comprising an apparatus having at least one opening, the apparatus is capable of holding a liquid or tissue sample, and further comprising one or more silica nanomembranes within the apparatus.

In accordance with an embodiment, the present invention provides a kit comprising one or more silica nanomembranes and instructions for use of the silica nanomembranes in isolation or purification of either DNA or RNA from a sample.

DETAILED DESCRIPTION OF THE INVENTION

In accordance with an embodiment, the present invention provides a silica nanomembrane comprising a polymer core and coated with a silicon dioxide layer, wherein the polymer core is heat shrunken and the silicon dioxide layer comprises a plurality of silica microstructures and nanostructures.

Figure 2:
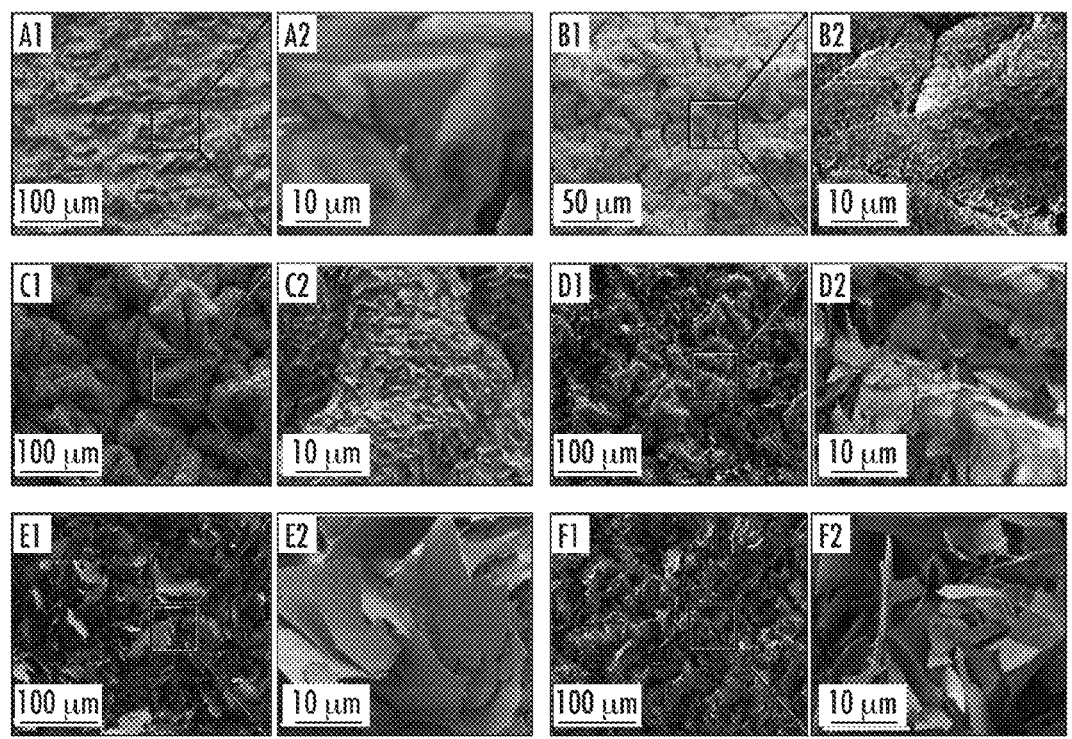
FIG. 2 depicts SEM images of the various silica nanomembrane surfaces showing that the hierarchical surface topography of microscale wrinkles topped by nanoscale flakes depends on the thickness of the deposited oxide. With a 2 nm silica layer, the membrane exhibited only microwrinkles rising slightly from the surface (FIG. 2A1). They are smooth without overlaying nanostructures (FIG. 2A2). At 20 nm, the micro-wrinkles grow taller and become more densely packed (FIG. 2B1). A close observation reveals that nano-wrinkles start to appear on the micro-wrinkles forming secondary hierarchical structures (FIG. 2B2). While at 50 nm, nanoflakes are observed alongside with nano-wrinkles overlaying on the micro-wrinkles (FIGS. 2C1 and 2C2). When the silica layer thickness is increased to 100 nm, a large number of silica flakes appear, ranging from tens of nanometers to micrometers (FIGS. 2D1 and 2D2). These flakes start to replace those nano-wrinkles as the thickness of silica layer increases, and they completely take the place of micro-wrinkles, when silica thickness exceeds 150 nm (FIGS. 2E1 and 2E2 for 150 nm, FIGS. 2F1 and 2F2 for 200 nm).

As used herein, the term "silica nanostructures" means three dimensional conformations of the silica on the polymer core which can comprise structures such as micro-wrinkles, nano-wrinkles and silica flakes, ranging from tens of nanometers to micrometers in size, examples of which can be seen in FIG. 2.

The term "silica" as used herein, means silicon dioxide and silicon dioxide derivatives, in particular $SiO_2$ crystals and other forms of $SiO_2$, for example diatoms composed of SiO$_2$, zeolites, amorphous silicon dioxide, glass powder, silicic acid, waterglass, and also aluminum silicates and activated silicates.

Figure 1:
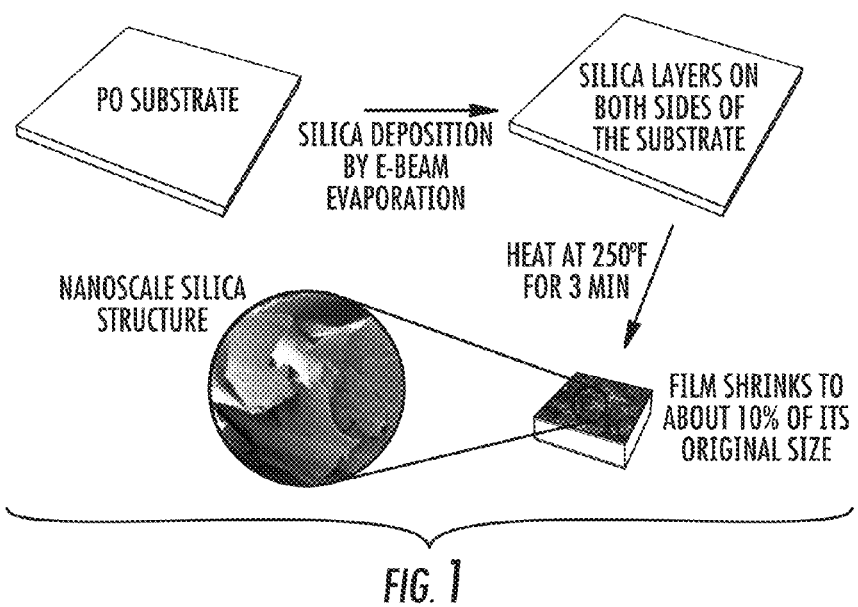
FIG. 1 is a schematic depicting the preparation of one embodiment of the silica nanomembranes of the present invention. A simple and inexpensive thermoplastic process is used to create a non-porous, rigid silica membrane with nanoscale topography for high yield, high purity, and high integrity DNA extraction.

The hierarchical pattern on the silica nanomembranes of the present invention is based on the thermally induced surface wrinkling of heat-shrinkable polymer film deposited with silica. The use of surface wrinkles caused by shrinking or swelling a pre-stretched soft polymer substrate coated with thin film of metals is one simple and low-cost method to fabricate nanomaterials. Due to different shrinkage or expansion coefficients between the polymer substrate and the stiff film, stress will accumulate within the film and eventually lead to spontaneous surface wrinkling (FIG. 1).

As used herein, the term "polymer" means any polymer substrate which is capable of heat shrinkage. In some embodiments, the polymers are thermoplastic polymers. As used herein, the term "thermoplastic" means a polymer which becomes pliable or moldable above a specific temperature and returns to a solid state upon cooling. Thermoplastics, can include, for example, polymers such as polymethyl methacrylate (PMMA), polycarbonate, polystyrene (PS), and cyclic polyolefin (PO) polymers.

The silica nanomembranes can be manufactured using the most commonly used polymer substrates, including, for example, pre-stretched thermoplastics, such as polymethylmethacrylate (PMMA), polycarbonate, polystyrene (PS), and cyclic polyolefin (PO) polymers. Silica is deposited on shrinkable PO films. After incubation at elevated temperature, the polymer film shrinks and the silica forms nanostructures due to the aforementioned mechanism (FIG. 2).

In some embodiments, the polymer core of the silica nanomembranes is selected from the group consisting of cyclic polyolefins, polystyrenes, polycarbonates, polymethyl methacrylate, polyvinyl chloride, polyethylene, fluorinated ethylene propylene, polytetrafluoroethylene, and polyvinylidene fluoride.

In some embodiments, the silicon dioxide layer of the silica nanomembranes has a thickness of between about 2 nm to about 500 nm.

In some embodiments, the polymer core of the silica nanomembranes has a shrunken thickness of between about 5 μm and 5 mm.

In some embodiments, the polymer core of the silica nanomembranes has pre-shrunken thickness of between about 5 μm and 500 μm.

In some embodiments, the silica comprising the silica nanomembranes is derivatized with other compounds or components known in the art. In some embodiments, the silica can be derivatized with aminopropyl groups, chloropropyl groups, octadecyl groups, octyl groups, quaternary ammonium groups, diethylaminoethyl group, sulfonic acid groups, phenyl groups, biotin, streptavidin, antibodies, or enzymes.

The exact nanostructures formed in the process of making the silica nanomembranes depends on its thickness of the coating or layer of silicon dioxide being deposited. As the silica layer gets thicker, the specific surface area of the silica nanomembrane is greatly enhanced, and concomitantly, the DNA binding capacity increases. Thus, the present inventive silica nanomembranes have higher DNA recovery yield compared with commercial silica columns and magnetic particles. The inventive silica nanomembranes are able to extract DNA from cultured human cells with high yield and comparable quality to the gold standard phenol-chloroform method.

The silica nanomembranes of the present invention can be fabricated into any shape suitable for specific purposes. The silica nanomembranes can be planar, or in a bead conformation. The silica nanomembranes can be circular, square or any particular shape. In one embodiment, the silica nanomembranes are circular and can fit into a test tube. In alternative embodiments, the silica nanomembranes can be adapted to fit in a column or pipette tip for flow-through analysis, or any other apparatus capable of holding a sample.

In an embodiment, the present invention provides a method for making a silica nanomembrane comprising: a) depositing onto a polymer film or core having an original size, a layer of silicon dioxide; and b) heating the composition of a) at a sufficient temperature and time to allow the polymer film or core to shrink, and wherein the shrinking of the polymer film or core creates silica microstructures and/or nanostructures on the surface of the layer of silica on the silica nanomembrane.

The silica nanomembranes are fabricated using simple, inexpensive, and inventive thermoplastic processes. In some embodiments, a range of about 2 nm to about 500 nm of silicon dioxide is deposited onto a 5 μm to about 500 μm thick polyolefin film by any known means of deposition. Examples of deposition methods include, but are not limited to chemical vapor deposition, electrophoretic deposition, dip-coating, physical vapor deposition, electron beam vapor deposition, sputtering, spin-coating, or liquid phase deposition.

The silica coated polyolefin film is then heat shrunk in an oven at a temperature sufficient to shrink the polymer. The temperature can vary as a function of the type of polymer used and the starting thickness of the polymer. Any heating means can be used such as infrared heater, heat gun, or resistive heating element.

In some embodiments, the polymer is heated in a temperature range of between 100° F. and 500° F. In an embodiment, the polymer is heated at 250° F.

The heating time for the shrinking process can also vary as a function of the type of polymer used and the starting thickness of the polymer.

In some embodiments the polymer is heated for between 10 seconds to 10 minutes. In an embodiment, the polymer is heated for 3 minutes.

The heat shrinking of the polymer causes the film to shrink in area by over 95% in size, while increasing in thickness, and creates a hierarchical structure of microscale folds topped by nanoscale flakes. The silica nanomembranes can then fabricated into a variety of shapes or sizes as needed for various applications.

In an embodiment, the silica nanomembranes can be punched into circles of varying diameter. In one embodiment, 6 mm diameter pieces can be used, which are capable of fitting into a common 1.5 ml tube, and which are capable of binding >150 μg of DNA each. Preliminary results have shown that the silica nanomembranes remain stable over at least 1 month (data not shown).

Figure 3:
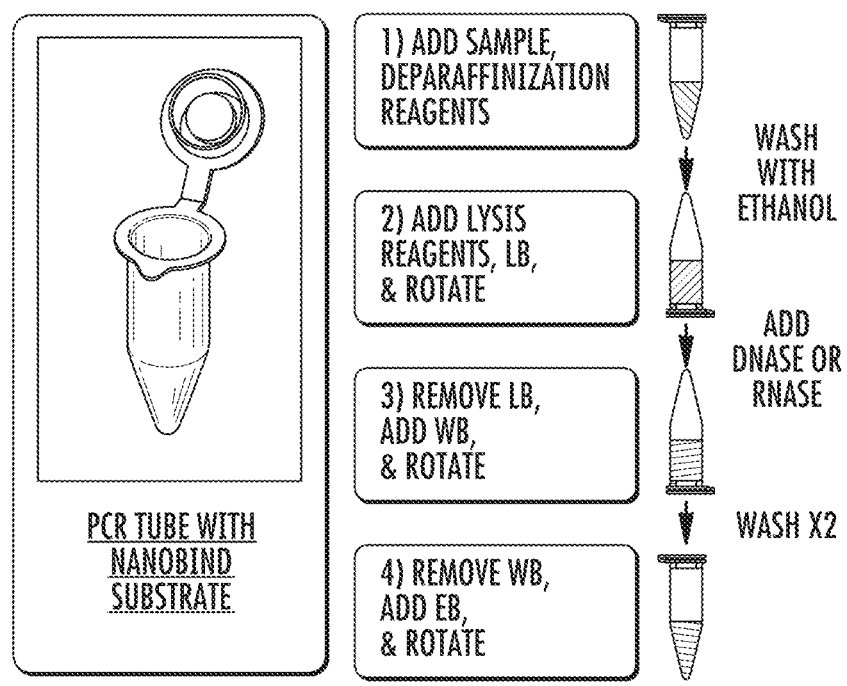
FIG. 3 shows a schematic of an embodiment of the present invention. The silica nanomembrane substrate (red, in cap) can be directly integrated into a PCR (1.5 ml) tube for streamlined DNA extraction and downstream analysis. Binding is performed by inverting and rotating the tube while elution is performed by up righting and low speed spin down.

It will be understood by those of skill in the art that the silica nanomembranes of the present invention can be molded or fabricated into a variety of shapes for different uses. In an embodiment, the silica nanomembranes can be made into a planar circular shape, using a punch to any diameter. In some embodiments, the diameter can be sized to fit various test tube or cell culture tubes or plates or dishes. As shown in FIG. 3, in one embodiment, a 6 mm circle of silica nanomembranes can fit into a cap of a 1.5 ml tube and be used for nucleic acid separations. These tubes can be premade and available as a kit which would include instructions for use, for example, along with reagents for sample preparation and clean up.

One of skill can envision other uses of the silica nanomembranes, for example in a column format. For example, in another embodiment, capillary tubes of glass or plastic of varying diameters could have their interior surface coated with the silica nanomembranes for a continuous flow method of extraction of nucleic acids.

In accordance with another embodiment, beads can be manufactured with the silica nanomembranes coating the exterior surface. These beads can then be placed in a tube, as with the circles, or in a column for a continuous flow method.

In accordance with yet another embodiment, the silica nanomembranes can be used in a microfluidic device. The microfluidic device is an apparatus which, in certain embodiments, comprises microfluidic channels with silica membranes embedded within. The silica nanomembranes may be attached at spatially defined locations on the device.

In accordance with yet another embodiment, the silica nanomembranes can be used in a chip format. The chip is an apparatus which, in certain embodiments, comprises a solid substrate comprising a plurality of discrete silica nanomembranes regions. The silica nanomembranes may be attached at spatially defined address on the substrate The silica nanomembranes may be attached to the chip in a wide variety of ways, as will be appreciated by those in the art. The silica nanomembranes may either be synthesized first, with subsequent attachment to the chip, or may be directly synthesized on the chip.

The solid substrate for the chip may be a material that may be modified to contain discrete individual sites appropriate for the attachment or association of the silica nanomembranes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. Similarly, the substrate may be flexible, such as a flexible foam, including closed cell foams made of particular plastics.

As described above, the chip and the silica nanomembranes may be derivatized with chemical functional groups for subsequent attachment of the two. For example, the chip may be derivatized with a chemical functional group including, but not limited to, amino groups, carboxyl groups, oxo groups or thiol groups. Using these functional groups, the silica nanomembranes may be attached using functional groups on the silica nanomembranes either directly or indirectly using linkers.

In some embodiments, the polymer film or core shrinks to between about 0.1% to about 75% of its original size when subjected to heat shrinking.

In accordance with an embodiment, the present invention provides a method for extracting nucleic acids from a sample comprising: a) obtaining a sample comprising nucleic acids; b) contacting the sample with a sufficient amount of silica nanomembranes; c) allowing the nucleic acids in the sample to adsorb onto the silica nanomembranes; d) washing the silica nanomembranes to remove any non-nucleic acid components; and e) desorbing the nucleic acids from the silica nanomembranes to obtain the isolated and purified nucleic acids from the sample.

The term "sample, or biological sample" as used herein, refers to any sample which comprises cells or cellular material, in particular cells, frozen cell pellets, fixed cells, feces/stool, buffy coat (i.e., white blood cell fraction of blood), ascites, swabs, in particular cheek or throat swabs, cervical swabs, sputum, organ punctates, sperm, tissue samples, fixed tissue samples, tissue sections of fixed or nonfixed tissue samples, in particular frozen sections and paraffin sections, in particular formalin-fixed paraffin sections, tumor material, biopsy samples, blood samples, in particular whole blood or blood fractions, cell suspensions, and in the broadest sense all samples which comprise cellular constituents, wherein both intact cells and cell constituents shall be comprised. Furthermore, the term also comprises other nucleic acid-containing, biological materials, such as, for example, blood serum or blood plasma, in particular virus-containing serum or plasma, HIV- and HCV-infected serum samples, secretions, CSF, bile, lymph fluid, urine. Similarly, it can be nucleic acid-containing materials which originate from biochemical or biotechnological processes and are to be subsequently purified.

In some embodiments, the method for extracting nucleic acids using the silica nanomembranes of the present invention comprises contacting the sample with a lysis and/or digestion solution prior to step a), followed by one or more washing steps to remove cellular debris and lysis and/or digestion components.

In some embodiments, the method for extracting nucleic acids using the silica nanomembranes of the present invention, includes at step a) contacting the nucleic acids with a chaotropic agent. This helps the nucleic acids to adsorb or bind to the silica microstructures and nanostructures on the nanomembrane.

In some embodiments, the method for extracting nucleic acids using the silica nanomembranes of the present invention, further comprises at step b) contacting the sample with a sufficient amount of silica nanomembranes in the presence of an aqueous alcoholic solution. It is well known that the aqueous alcoholic solution helps precipitate the nucleic acids from the other cellular or tissue components in the sample.

In some embodiments, the method for extracting nucleic acids using the silica nanomembranes of the present invention comprises two, or three or more washing steps, such as at step d), for example. These washes can include buffers, alcohols, or other reagents known to be suitable for use in isolation and purification of nucleic acids.

For the purification of DNA, preference is given to adding RNase in a biologically effective amount to the sample, whereby RNA can be digested and the intact DNA can be isolated from the sample. The RNase digestion can be carried out at different times during the extraction, at the earliest after lysis, and at the latest after the elution at the end of the purification. However, preference is given to detecting the DNA in the presence of the copurified RNA, i.e., by omitting the RNase step or by using buffer conditions which enable selective isolation of DNA with exclusion of the RNA.

For the isolation of RNA, preference is given to adding a DNase in a biologically effective amount to the sample. This results in DNA being "digested" and going into solution, while the undigested RNA can be isolated from the solution. The DNase digestion can be carried out at different times during the extraction, at the earliest after lysis, and at the latest after the elution at the end of the purification.

The methods of the present invention can be used to enrich a sample in a particular type of nucleic acid, e.g. DNA or RNA. For example, at step d) one can add a DNAse to remove DNA from the nucleic acids in the sample and enrich the sample in RNA. Likewise, one of skill can add an RNAse to the sample at step d) to remove RNA from the nucleic acids in the sample and enrich the sample in DNA.

The methods of the present invention can be used to enrich a sample in a particular type of nucleic acid, e.g. DNA or RNA or long nucleic acids or short nucleic acids. For example, during the binding step c) and washing step d), the percentage of alcohol in the buffers can be used to adjust solubility that will lead to preferred binding and elution of a specific species. Salts may also be used to preferentially extract a particular type of nucleic acid by adjusting the relative solubilities.

In some embodiments, the method for extracting nucleic acids using the silica nanomembranes of the present invention comprises a drying step after step d).

It will be understood by those of skill in the art that the nucleic acids which are bound or adsorbed on the silica nanomembranes of the present invention can be desorbed from the nanomembranes by the use of any elution solution known in the art. A typical elution solution can be a buffer comprising a mixture of (0.5 M) ammonium acetate, 10 mM magnesium acetate and 1 mM EDTA, for example. Another typical elution solution can be a buffer comprising a mixture of 10 mM Tris base and 1 mM EDTA, for example. Yet another typical elution solution can be water.

In accordance with another embodiment, the present invention provides a method for extracting nucleic acids from formalin fixed paraffin embedded (FFPE) samples comprising: a) obtaining a FFPE sample comprising nucleic acids; b) deparaffinizing the sample; c) contacting the sample with a sufficient amount of silica nanomembranes; d) allowing the nucleic acids in the sample to adsorb onto the silica nanomembranes; e) washing the silica nanomembranes to remove any non-nucleic acid components; and f) desorbing the nucleic acids from the silica nanomembranes to obtain the isolated and purified nucleic acids from the sample.

The methods for extracting nucleic acids from FFPE samples will be understood to have the same basic principles as described in the non-FFPE sample extraction methods described above. The basic difference being the addition of a deparaffinization step. Deparaffinization of FFPE samples is known in the art.

In some embodiments, the deparaffinization of the FFPE sample comprises contacting the sample with an organic solvent to dissolve the paraffin. Suitable examples of organic solvents include, but are not limited to, xylene, hexadecane, toluene, 5-chloro-2-methyl-4-isothiazolin-3-one, 5-chloro-2-methyl-4-isothiazolin-3-one; a terpene or isoparaffinic hydrocarbon, and 2-butoxyethanol. In other embodiments, mineral oil can be used, with or without heating the sample to dissolve the paraffin. In an alternative embodiment, deparaffinization of the FFPE sample can also be performed with heating the sample alone without any organic solvents. One can add buffer to the sample, heat the sample for a sufficient time to melt the paraffin, and then centrifuge the sample while heated. The melted paraffin will rise to the top and solidify.

In some embodiments, after the deparaffinization step, the method comprises removing the organic solvent, and washing the sample. The remainder of the method would proceed as with the non-FFPE sample methods described herein.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

In an embodiment, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids isolated in embodiments of the present invention can be constructed based on chemical synthesis and/or enzymatic ligation reactions using procedures known in the art. See, for example, Sambrook et al. (eds.), *Molecular Cloning, A Laboratory Manual*, $3^{rd}$ Edition, Cold Spring Harbor Laboratory Press, New York (2001) and Ausubel et al., *Current Protocols in Molecular Biology*, Greene Publishing Associates and John Wiley & Sons, NY (1994). For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The term "isolated and purified" as used herein means a nucleic acid that is essentially free of association with other proteins or polypeptides, e.g., as a naturally occurring protein that has been separated from cellular and other contaminants by the use of the silica nanomembranes of the present invention.

"Identical" or "identity" as used herein in the context of two or more nucleic acids or polypeptide sequences may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

The term "cellular", as used herein, can refer to both prokaryotic cells and eukaryotic cells.

The term "lysing the sample" comprises the breaking open of cells or cellular structures in the sample. It comprises in particular mechanical lysis methods (e.g., ultrasound), thermal lysis (e.g., freeze-thaw cycles, heating the sample), and chemical lysis (e.g., with detergents). However, the expression "lysing the sample" is not restricted to cells and can also refer to the release of nucleic acids by the described methods from noncellular, biological structures or complexes.

The term "chaotropic conditions" refers to solvent conditions in the presence of chaotropic agents or compounds. Chaotropic agents or compounds are compounds which change or disrupt the secondary structure, tertiary structure, and quaternary structure of proteins, nucleic acids, and protein-nucleic acid complexes while the primary structure remains intact. In solution, under chaotropic conditions, the intramolecular interactions of biological molecules, in particular proteins, protein-nucleic acid complexes, and nucleic acids, are disrupted, since chaotropic compounds interfere with stabilizing intramolecular interactions in biological molecules, for example hydrogen bonds, van der Waals forces, and hydrophobic effects. Chaotropic compounds usually have large-volume ions which, owing to their size, can interfere with the intramolecular interactions and reduce the polarity of the solvent as a result, thereby disrupting intermolecular and intramolecular hydrogen bonds. Consequently, many proteins precipitate; however, the helical structure of double-stranded nucleic acid segments is maintained. By adding chaotropic compounds to cell lysates or cell suspensions, proteins can be precipitated while nucleic acids remain in solution. Under chaotropic conditions, the binding of nucleic acids to silicon dioxide-based matrices is greatly favored. Chaotropic compounds comprise, for example, high molecular weight urea solutions (e.g., 6 to 8 mol/l urea), guanidinium salt solutions (e.g., 6 mol/l guanidinium chloride), high molecular weight lithium salts (e.g., 4.5 mol/l lithium perchlorate). Chaotropic anions comprise the anions $F^-$, $PO_4^{3-}$, $SO_4^{2-}$, $CH_3COO^-$, $Cl^-$, and in particular $Br^-$, $I^-$, $NO_3^-$, $ClO_4^-$, $SCN^-$, and $Cl_3CCOO^-$. Chaotropic cations comprise the cations $Li^+$, $Mg^{2+}$, $Ca^{2+}$, $Ba^{2+}$, and in particular the guanidinium cation $[CH_6N_3]^+$. Chaotropic compounds preferred for nucleic acid isolation are guanidinium isothiocyanate ($[CH_6N_3]^+SCN^-$) and guanidinium chloride.

The term "separation" as used herein, means removing as far as possible all biological or chemical substances or components which are not the actual target of the isolation—i.e., which essentially are not nucleic acids. In particular, the separation of these substances serves to avoid interference or disturbances during the actual binding, enrichment, purification, and subsequent detection of the target molecules.

The term "cellular debris" as used herein, means all biological components which are not the primary target of nucleic acid isolation and are to be separated from the actual target molecules by a purification or negative selection step. After lysis of a cellular sample, this includes cell constituents which are insoluble and difficult to lyse, particularly in an aqueous solution, such as, for example, necrotizing tissue constituents, bone or lime structures, in particular microcalcifications, but also as well burst or morphologically altered erythrocytes, wart-like and papilloma-like tissue structures, and also specific bacteria which have a complex, difficult-to-lyse sugar coat (e.g., mycobacteria). Moreover, this includes proteins, membrane constituents, structures cross-linked particularly due to fixing, etc. In individual cases, it can, however, also be water-soluble components which are released according to the above-described lysis processes and are to be separated. An example is the hemoglobin which is released in large amounts and in a molar excess with respect to nucleic acids, after the lysis (e.g., by means of hypotonic buffer conditions) of erythrocytes, and which is to be separated prior to further processing of the bodily sample.

The term "magnetic particles" as used herein, means both organic and inorganic magnetic particles.

The term "lysis buffer" includes buffers which comprise at least one substance which is able to cause or favor the disruption of a cell, a cell system, cell constituents, or other biological complexes or structures. The substances are especially often selected from the group of detergents (Triton X-100, SDS, or the like) and enzymatic reagents, such as proteinase K in particular. Also included is the use of reagents from the group of aqueous, buffered or unbuffered solutions (water in the simplest case). In a lysis buffer, one or more components may be combined from one or both groups or with one another.

In accordance with a further embodiment, the present invention provides a method for extracting nucleic acids from a sample comprising: a) obtaining a sample comprising nucleic acids; b) contacting the sample with a sufficient amount of silica nanomembranes; c) allowing the nucleic acids in the sample to adsorb onto the silica nanomembranes; d) washing the silica nanomembranes to remove any non-nucleic acid components; and e) desorbing the nucleic acids from the silica nanomembranes to obtain the isolated and purified nucleic acids from the sample.

DNA Extraction with Silica Nanomembranes.

As depicted in FIG. 3, in some embodiments of the methods of the present invention, a chaotropic buffer such as AL (Qiagen, guanidine hydrochloride solution) or similar buffer, and a proteinase, such as proteinase K, can be added to the cells and incubated at about 50-60° C. for between about 1-2 hours. The guanidine and proteinase K buffer lyses the cells and enables DNA to subsequently bind. An alcoholic solution, such as ethanol or isopropanol and the silica nanomembranes were then added to precipitate and bind the DNA. The solution was rotated and incubated at room temperature for a time between 10 minutes to about an hour to allow nanomembrane binding to occur. The liquid was then pipetted out, and the membranes were washed twice with wash buffers WB1 and WB2 (Qiagen, ethanol stringency wash) or any other similar wash. Next, the membranes were air dried to remove any residual ethanol. Finally, an elution buffer such as (Qiagen, TE buffer) was added and incubated at 70° C. for between 30 minutes to about 1 hour to elute and desorb the DNA from the silica nanomembranes. This allows obtaining high integrity, high yield, and high purity DNA extractions, and substantial RNA was co-purified with the DNA. In alternative embodiments, cells can be lysed using heat, surfactants such as Triton, Tween, and SDS, and chaotropes such as guanidine hydrochloride. The wash buffers are used to wash away soluble contaminants such as salts and proteins. They typically contain 70% ethanol and may contain chaotropes such as guanidine hydrochloride and/or detergents such as Tween to denature and wash away proteins. Alternatively, isopropanol wash solutions may be used. The elution buffers typically consist of TE buffer or DI water. Elution at elevated temperature for longer time can result in higher extraction yields.

It will be understood by those of ordinary skill in the art, that the methods for nucleic acid isolation using the silica nanomembranes of the present invention, disclosed throughout the specification, can include additional washes between steps to remove any cellular debris and lysis and/or digestion components.

FFPE DNA Extraction with Silica Nanomembranes.

The first step in the FFPE extraction methods of the present invention involves deparaffinization (i.e. solubilization of the paraffin wax). In some embodiments, slices of thick FFPE tissue between 5-10 μm in thickness, are placed in 1.5 mL tubes and 1 mL of an organic solvent, such as xylene is added (Pathol. Res. Pract., 204, 633 (2008); Methods Mol Biol 724, 161 (2011)). The xylene is then removed and the sample pellet is washed with graded ethanol solutions to eliminate xylene and rehydrate the DNA. In other embodiments, the deparaffinization methods can be varied by altering the xylene concentration, incubation times, and wash protocol to ensure that all the paraffin is removed and xylene carry through is minimal.

Cell lysis can then be performed by adding proteinase K (New England Biolabs) and a pH 7.5 TE buffer containing 6M Guanidine HCl to the deparaffinized pellets and incubating at 55° C. for about 1 hour. The proteinase K will lyse the cells and release the nucleic acids while the chaotropic salt Guanidine HCl enables DNA binding to the silica nanomembranes substrate. Heating during this step will also reverse cross-linking by formalin. After incubation, ethanol will be added to the sample to precipitate the DNA and facilitate binding to the membrane. The samples will then be washed twice with 70% ethanol and air dried to eliminate any residual ethanol. The nucleic acids are then desorbed from the silica nanomembranes using elution buffers or similar means.

In preliminary experiments, co-purification of both DNA and RNA was obtained. To eliminate RNA contamination, RNase H (New England Biolabs) can be added to the sample immediately after the lysing step to digest RNA. The digested RNA will not bind the Nanobind substrate and will be washed away. Ethanol percentage has a large effect on the size of DNA/RNA fragments that bind silica due to the different solubility of small vs. large fragments. The ethanol content of the binding and wash buffers can be varied in the digestion protocols to ensure that all RNA is removed.

RNA FFPE Extraction Methods.

As RNA degradation occurs much more readily and quickly than DNA degradation, archived FFPE samples are unlikely to contain long RNA molecules that can be used for mRNA expression profiling, but may contain intact small RNA, such as miRNA, that can be extracted and profiled. Additionally, fresh FFPE samples are emerging as a viable and less expensive alternative to fresh frozen samples for diagnostics applications. The deparaffinization, cell lysis, and RNA binding is performed the same as for FFPE DNA samples above, however, rather than performing an on-substrate RNase digestion, a DNase I (New England Biolabs) digestion will be performed after proteinase K digestion. The digested DNA will then be carried away by the ethanol based wash buffers. Ethanol percentage has a large effect on the size of DNA/RNA fragments that bind silica due to the different solubility of small vs. large fragments. The DNase digestion protocol (time, temperature, etc) and the ethanol content of the binding and wash buffers are varied to ensure that the digested DNA is entirely washed away.

DNA and RNA Profiling in FFPE Tissues.

PCR forms the backbone of molecular analysis techniques. While these methods typically have high detection sensitivity, PCR is extremely sensitive to background contaminants and requires high purity starting material. DNA and RNA isolated from FFPE tissues using the silica nanomembranes can be used in prototypical epigenetic and genetic profiling assays, including, for example, methylation specific qPCR, qPCR, and RT-qPCR.

It will also be understood by those of ordinary skill in the art, that the compositions, devices and methods using the silica nanomembranes of the present invention can be combined with any other analytic techniques useful for isolating, purifying and analyzing nucleic acids known in the art.

In accordance with an embodiment, the present invention provides a device for extracting nucleic acids from a sample comprising an apparatus having at least one opening, the apparatus is capable of holding a liquid or tissue sample, and further comprising one or more silica nanomembranes within the apparatus. In some embodiments, the device is a container having a closure or lid. In some embodiments, the device is a tube, such as a test tube or 1.5 ml centrifuge tube. There is no limit on the size of the tube comprising the silica nanomembranes of the present invention. One of skill in the art would understand that the silica nanomembranes can be included into the interior of an apparatus, such as a column and affixed to the interior surface, for example.

In accordance with an embodiment, the present invention also provides a kit comprising one or more silica nanomembranes and instructions for use of the silica nanomembranes in isolation or purification of either DNA or RNA from a sample. Such a kit would be provided in a container with other reagents or materials necessary to perform the nucleic acid isolation and purification. The kits of the present invention can also include a device or apparatus comprising the silica nanomembranes.

Examples

Silica Nanomembrane Fabrication. An example of a fabrication procedure for an embodiment of the silica nanomembranes of the present invention is shown in FIG. 1. Silica was deposited onto both sides of the PO film using electron beam (E-beam) physical vapor deposition with deposition rate of 2 Å/s. As described above, the silica can also be deposited by sputtering, low pressure chemical vapor deposition, plasma enhanced chemical vapor deposition, electrochemical methods, spin coating with spin on glass, and liquid deposition. Then the silica-coated PO film was baked in an oven at 2° F. for 3 minutes to induce shrinking hence surface wrinkling. The resultant film was retracted to smaller than 10% of its original size through heat-induced shrinkage, and its surface exhibited hierarchical micro- and nanostructures that were verified under scanning electron microscope (SEM).

These overlaying silica hierarchical structures vary from nano to micro scale depending on the thickness of silica deposited, as shown in FIG. 2. With a 2 nm silica layer, the membrane exhibited only micro-ridges rising slightly from the surface (FIG. 2A1). They are smooth without overlaying nanostructures (FIG. 2A2). At 20 nm of thickness, the micro-ridges of silica grow taller and become more densely packed (FIG. 2B1). A close observation reveals that the silica nano-wrinkles begin to appear on the ridges forming secondary hierarchical structures (FIG. 2B2). With a 50 nm silica layer, nano-chips are observed alongside with nano-wrinkles overlaying on the micro-ridges (FIGS. 2C1 and 2C2). When the silica layer is increased to 100 nm, a large number of silica flakes appear ranging from tens of nanometers to micrometers (FIGS. 2D1 and 2D2). These flakes begin to replace those nano-wrinkles as the thickness of silica layer increase and completely take the place of micro-ridges when silica deposition exceeds 150 nm (FIGS. 2E1 and 2E2 for 150 nm, FIGS. 2F1 and 2F2 for 200 nm). These nano-flakes interweave with each other to form secondary structures on micro scale thus the hierarchical patterns remains. As the silica layer increases, more nano-flakes emerge and their micro-scale secondary structures become increasingly well-organized, resulting in larger overall silica surface areas.

The hierarchical silica pattern, from nano to micro scale, on the nanomembranes of the present invention, significantly enlarges the specific surface area of silica thus enhance its DNA absorption capability as a novel substrate for solid phase extraction. To evaluate the efficiency of the silica nanomembrane as the solid substrate for DNA isolation, the recovery yield of re-isolated control DNA using the nanomembrane was compared with that using commercial magnetic silica beads.

Figure 4:
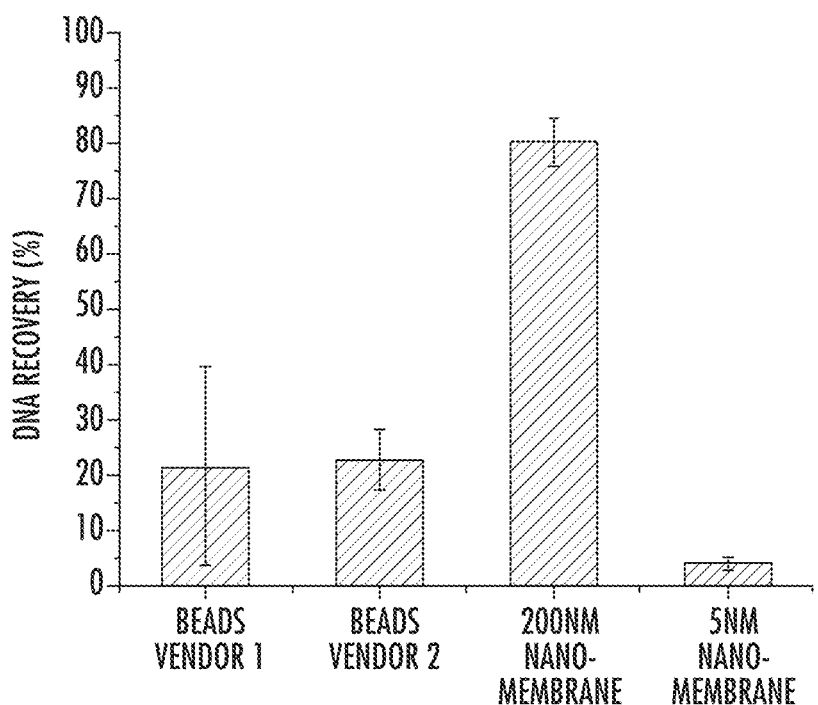
FIG. 4 compares DNA extractions performed using magnetic beads from two different vendors, a silica nanomembrane with 200 nm of oxide and a silica nanomembrane with 5 nm of oxide. The nanomembrane with 200 nm of oxide shows the highest DNA recovery yield due to the high surface area. 4 µg of commercially purified human genomic DNA was used as a starting material.

Isolation of DNA using Silica Nanomembranes. Using an embodiment similar to what is depicted in FIG. 3, using 4 μg commercial genomic DNA input, about 3.2 μg (80%) of DNA was recovered using the nanomembranes having a 200 nm silica layer (FIG. 4), while only about 0.8 μg (20%) was recovered using commercial silica magnetic beads. However, not all the nanomembranes have the comparable performance. Under the same conditions, the nanomembranes with only a 5 nm silica layer exhibited virtually no DNA recovery, which can be explained by the surface structure difference on the nanomembranes resulted from different silica thickness, as shown in FIG. 2. A thicker deposition of silica induces rougher surface thus larger specific surface area, and leads to increasing DNA adsorption capacity on the nanomembrane.

Figure 5:
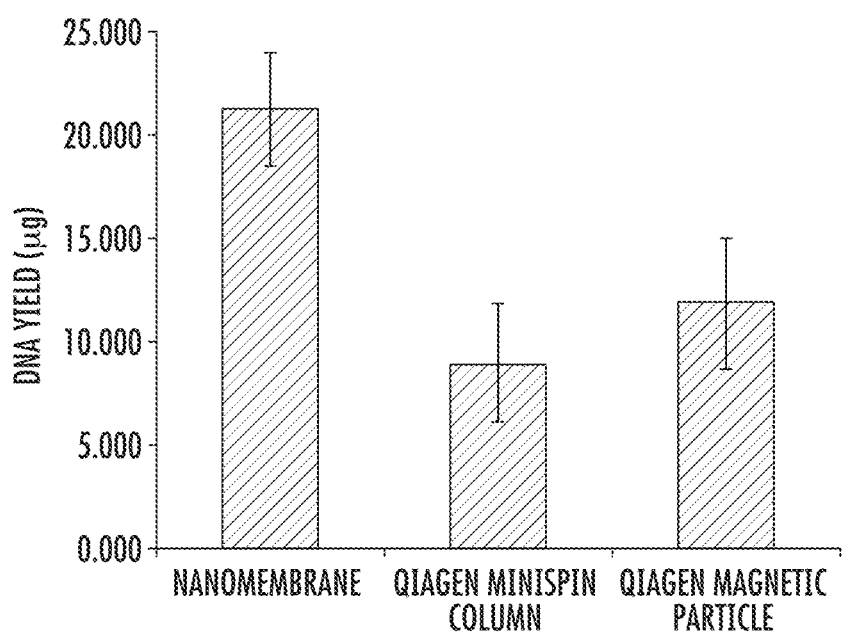
FIG. 5 shows that comparisons of extractions performed using Qiagen columns, Qiagen beads, and the silica nanomembranes of the present invention, indicate that the silica nanomembranes are capable of higher DNA binding capacity. About $3-4 \times 10^6$ cells were used as a starting material. This number of cells contains approximately 20-25 µg of DNA.

DNA extraction was performed on cultured cells utilizing the silica nanomembranes of the present invention. We were able to extract 11±4 μg of genomic DNA from about $2\times10^6$ cells. This yield is comparable to the gold standard Phenol-Chloroform method. The DNA yield from cultured cells using the inventive nanomembranes was also compared to methods using commercial kits such as a spin column and silica magnetic beads. Using about $3\sim4\times10^6$ cells, about 21.2±2.6 μg of genomic DNA was recovered using the inventive nanomembranes. In comparison, about 9.0±2.9 μg of genomic DNA was recovered using a spin column, and 11.9±3.1 μg of genomic DNA was recovered using magnetic beads under the same conditions (FIG. 5). The DNA yield using the spin-column and magnetic particles was only about 42% and 56% of the DNA yield using the inventive nanomembranes respectively.

Figure 6:
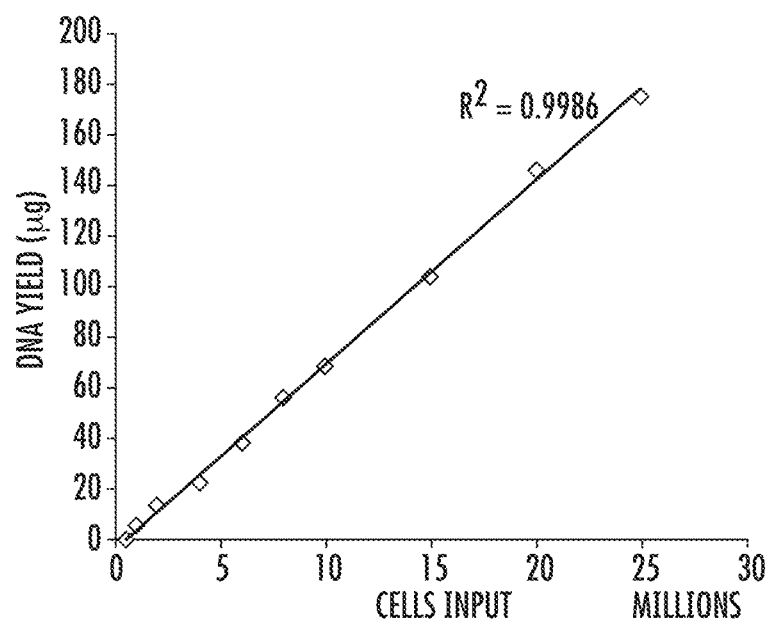
FIG. 6 shows the linearity of DNA binding of the silica nanomembranes of the present invention. In an embodiment, a 6 mm piece of Nanobind was used to isolate DNA from a starting input of between 1 to 25 million colorectal cancer cells. The amount of extracted DNA varied linearly with input cells across this range indicating that even at 25 million cells, the membrane had yet to saturate with DNA. This is 5-30 fold greater than standard columns can accommodate.

The hierarchical micro- and nanostructures on membrane significantly enlarges the total surface area of silica for DNA adsorption, and thus, enhances its DNA binding capacity. To evaluate the DNA binding capacity of the silica nanomembrane, the membrane was cut into small round pieces with a diameter of about 6 mm, and utilized one piece in a 1.5 mL tube to extract DNA from different amount of cultured cells ranging from $0.5\times10^6$ to $2.5\times10^7$. As shown in FIG. 6, the silica nanomembranes of the present invention presented a stable DNA yield, as a solid-phase substrate for DNA extraction from cultured cells, in a wide range of sample amounts. The tiny 6 mm piece of nanomembrane with an area of only 28 mm$^2$ was able to efficiently recover genomic DNA from as many as 25 million cells in a single 1.5 mL tube. This indicates that the silica nanomembranes of the present invention are able to capture as much as 6 μg of genomic DNA per square mm, due to its significantly enlarged silica surface area. In comparison, most commercial kits using spin columns or magnetic beads could only process up to $2\times10^6$ cells per tube. Considering that the capacity curve in FIG. 4 hasn't reached the plateau with such a high input, the silica nanomembranes have great potential for large quantity DNA processing in single tube.

Figure 7:
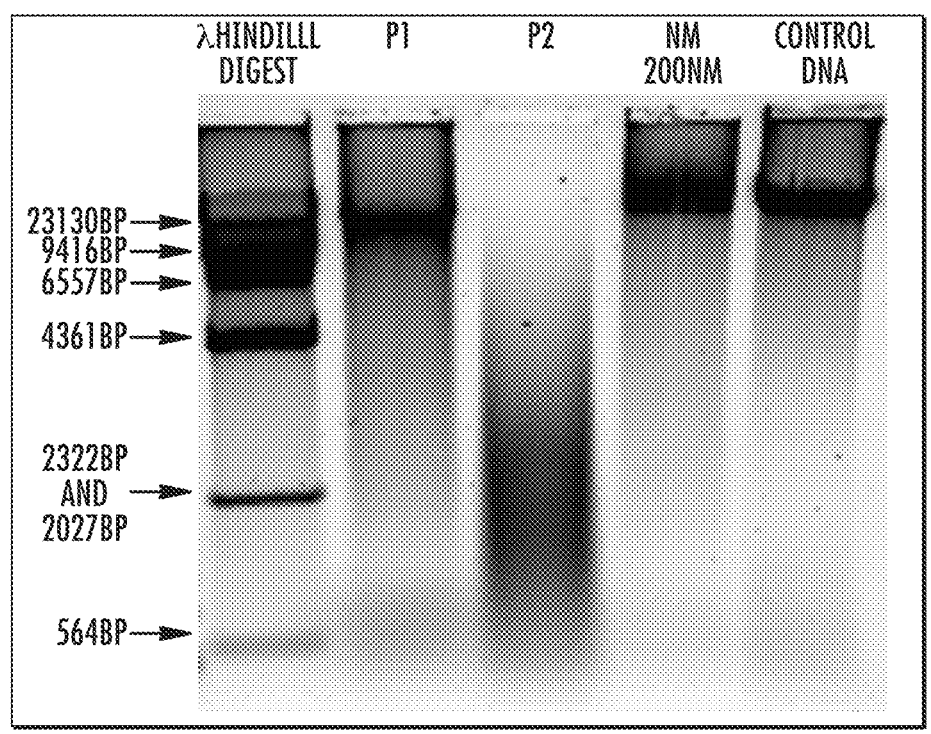
FIG. 7 depicts that there is less DNA shearing with the silica nanomembrane than with other commercial methods of DNA isolation. Compared to control DNA obtained through phenol chloroform method, DNA isolated using magnetic particles (P1 and P2) were sheared into smaller fragments. The greatest DNA shearing occurred in DNA isolated using P2 (about 100 nm in diameter) particles. In contrast, DNA isolated using silica nanomembrane retained integrity that matched the control DNA.
Figure 8:
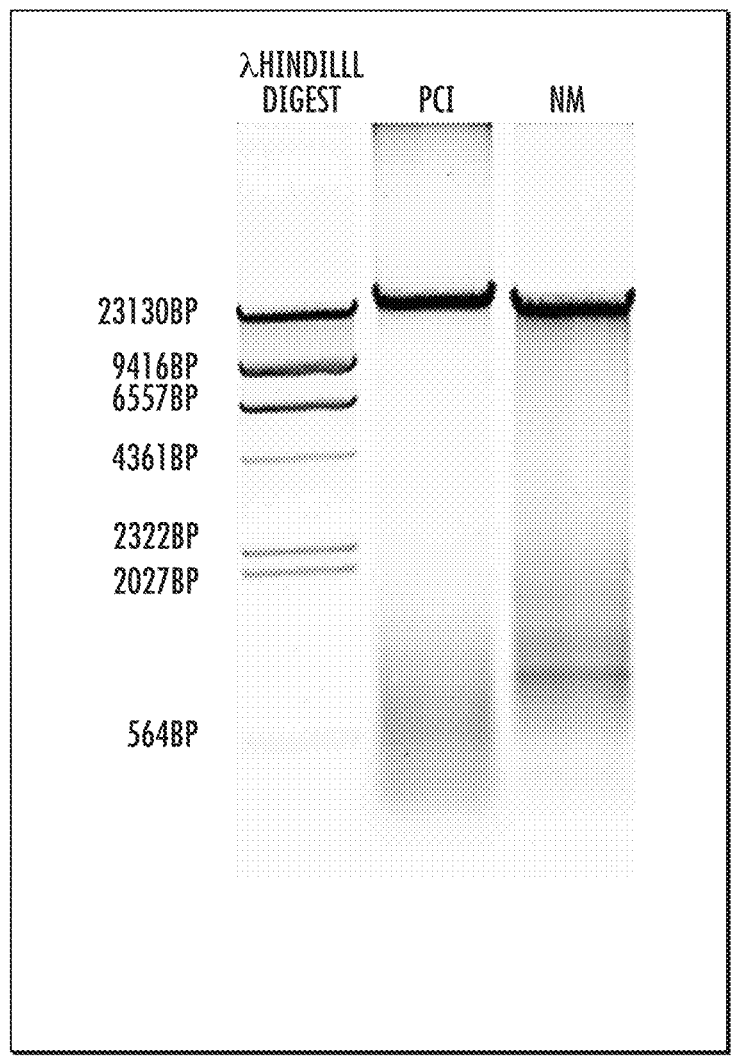
FIG. 8 compares the integrity of DNA isolated using the silica nanomembranes of the present invention compared to phenol-chloroform extraction. Gel electrophoresis proves that the silica nanomembrane extraction yielded high molecular weight DNA, over 23 kb, comparable with those extracted by phenol chloroform method.

Comparison of DNA Isolated by Silica Nanomembranes with Magnetic Particles. DNA isolated by magnetic particles is often sheared into small fragments due to the mechanical stress. The phenomenon is observed by running the re-isolated DNA in gel electrophoresis (FIG. 7). Compared to control DNA obtained through phenol chloroform method, DNA isolated using magnetic particles (P1 and P2) were sheared into smaller fragments. DNA isolated using P2 (about 100 nm in diameter) was sheared most significantly. In contrast, DNA isolated using the inventive silica nanomembrane retained high integrity. The integrity of DNA extracted from cultured cells using the silica nanomembrane was also compared with DNA extracted using the phenol-chloroform method. Gel electrophoresis shows that the silica nanomembrane extraction yielded high molecular weight DNA, over 23 kb, comparable with those extracted by phenol chloroform method (FIG. 8).

Figure 9:
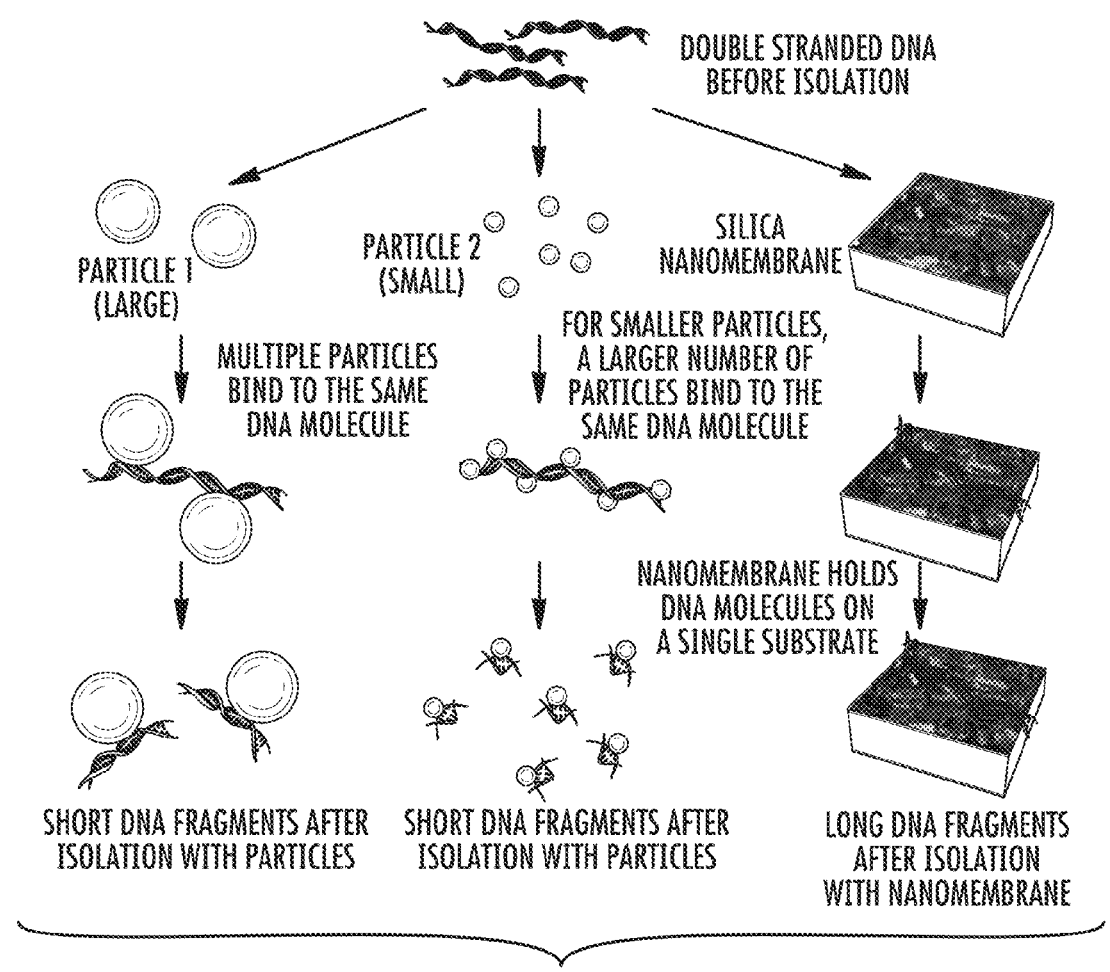
FIG. 9 is a schematic illustration of how DNA can become sheared using magnetic microparticle methods vs. the silica nanomembranes of the present invention.

Without being held to any particular theory, to explain why DNA molecules isolated with silica nanomembrane maintain their integrity, whereas those isolated with particles are sheared, it is thought that multiple particles would bind to a single long DNA (FIG. 9). These particles move independently, stretch, and eventually break the long DNA strand into short fragments. Smaller particles allow more particles to bind to the same DNA strand, leading to more breaking points, hence even smaller DNA fragments. In contrast, when DNA molecules are adsorbed onto the silica nanomembrane, although the active surface structure is in the nanoscale dimension, the physical dimensions of the nanomembrane are in millimeters. As a result, long DNA strands are able to bind to the same planar membrane, preventing them from being stretched and broken. Therefore, DNA isolated using nanomembrane are able to retain the integrity.

Figure 10:
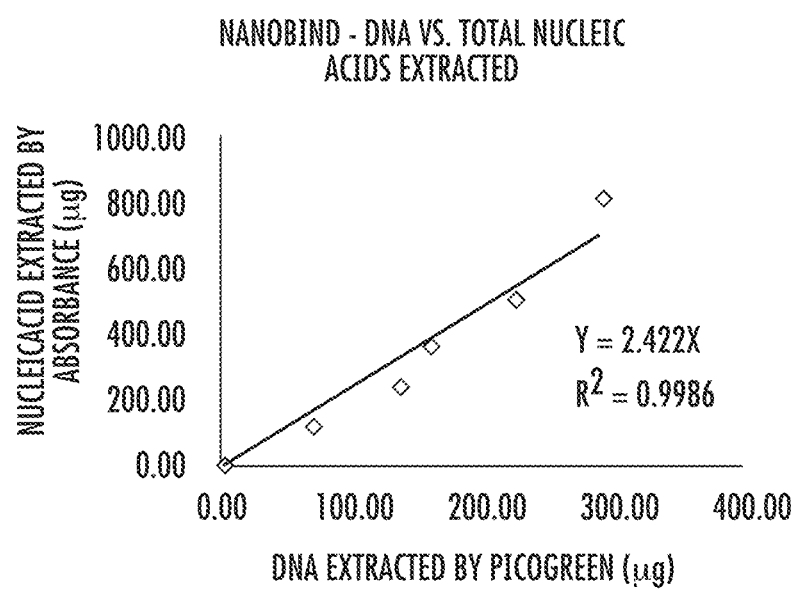
FIG. 10 depicts isolation of nucleic acids from between 1 to 25 million input cells and quantified using PicoGreen (x-axis) and absorbance (y-axis). The difference between the measurements indicates that both RNA and DNA were co-extracted. Approximately 60% of the extracted nucleic acids consist of RNA.

FFPE Extraction Methods. About 20 pieces of 7 μm thick FFPE slices taken from colon polyps were placed in a 1.5 mL tube, deparaffinized using xylene/graded ethanol, lysed with proteinase K, and subject to DNA extraction using a single 6 mm piece of silica nanomembrane. The extracted DNA was then washed and eluted in TE buffer. The experiment was performed in duplicate. PicoGreen measurements indicate that the silica nanomembrane was successful in isolating 201±2 ng of DNA. This demonstrates that the silica nanomembrane is fully compatible with, and has great potential in facile and high performance FFPE nucleic acid extraction. Our preliminary experiments used extraction chemistry that isolated large amounts of both DNA and RNA. This is evident when comparing extraction yields obtained from absorbance measurements, which include DNA and RNA, vs. those obtained using PicoGreen measurements, which include DNA only (FIG. 10). These results indicate that approximately 60% of the extracted nucleic acids are RNA.

Figure 11:
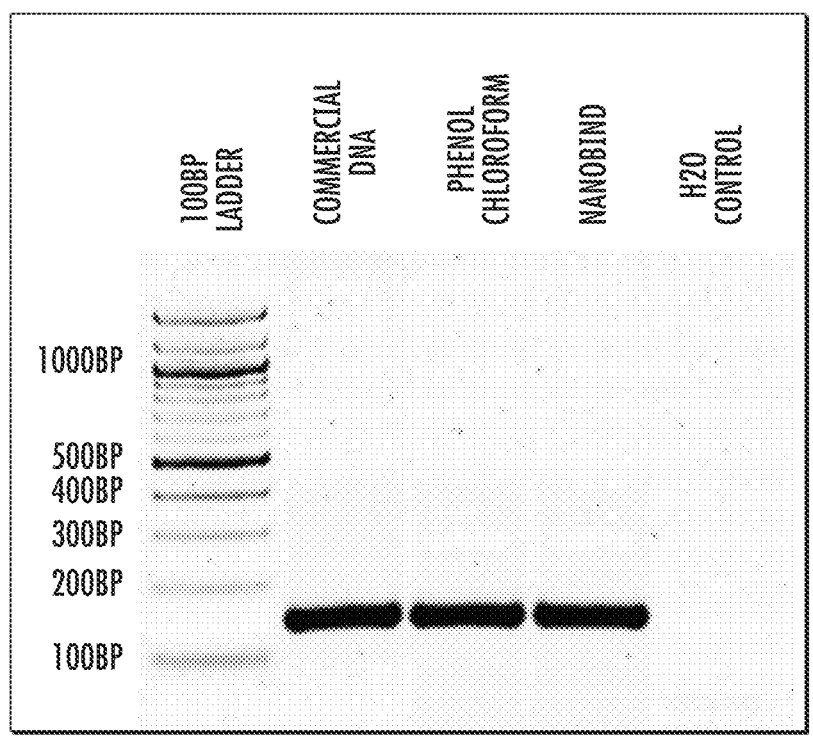
FIG. 11 is a gel showing DNA extracted using the silica nanomembranes of the present invention are suitable for use in PCR. PCR was performed on commercial genomic DNA and on DNA extracted using Nanobind and phenol chloroform. All 3 samples successfully amplified the expected 148 bp GAPDH target, indicating successful extraction and PCR compatibility.

PCR Analysis of DNA Extracted using Silica Nanomembranes. Preliminary experiments were performed to verify that the DNA extracted using the silica nanomembrane was free of contaminants and suitable for PCR. PCR was performed using primers to amplify a 148 bp region of the human GAPDH gene. DNA isolated from ovarian cancer cells using silica nanomembrane was compared against DNA extracted using phenol-chloroform and commercially purchased human genomic DNA. In all cases, the expected product was cleanly amplified, indicating that the silica nanomembrane was successful in isolating pure DNA that was free of PCR inhibitors (FIG. 11).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for extracting nucleic acids from a sample comprising:

a) contacting the sample comprising nucleic acids with a sufficient amount of silica nanomembranes, wherein the silica nanomembranes comprise a heat shrunken polymer core coated with a silicon dioxide layer, and wherein the silicon dioxide layer comprises a surface structure comprising wrinkle structures having a length from about 10 nm to about 100 μm and/or discreet substantially planar flakes having a length from about 10 nm to about 100 μm; and b) purifying said nucleic acids from the sample.

2. The method of claim 1, wherein the sample is selected from the group consisting of: a cell, tissue, blood, serum body fluid, formalin-fixed paraffin embedded tissue, enzymatic reaction, plant, bacteria, and viral particle.

3. The method of claim 1, further comprising at step a) deparaffinizing the sample.

4. The method of claim 3, wherein washing comprises two or more washes.

5. The method of claim 3, further comprising a drying step after washing.

6. The method of claim 3, wherein deparaffinization comprises contacting the sample with an organic solvent.

7. The method of claim 6, wherein the organic solvent is selected from the group consisting of: xylene, mineral oil, hexadecane, toluene, 5-chloro-2-methyl-4-isothiazolin-3-one, 5-chloro-2-methyl-4-isothiazolin-3-one; a terpene or isoparaffinic hydrocarbon, and 2-butoxyethanol.

8. The method of claim 6, wherein step a) further comprises removing the organic solvent, and washing the sample.

9. The method of claim 1, further comprising step c) desorbing the nucleic acids from the silica nanomembranes to obtain the isolated and purified nucleic acids from the sample.

10. The method of claim 9, wherein at step c) the desorption of the nucleic acids from the silica nanomembranes is by application of an elution solution.

11. The method of claim 1, wherein purifying said nucleic acids comprises washing the silica nanomembranes to remove any non-desired components.

12. The method of claim 1, further comprising contacting the sample with a lysis and/or digestion solution prior to step a).

13. The method of claim 1, wherein at step a) the nucleic acids are contacted with a chaotropic agent.

14. The method of claim 1, further comprising at step a) contacting the sample with the sufficient amount of silica nanomembranes in the presence of an aqueous alcoholic solution.

15. The method of claim 1, further comprising adding to the sample a DNAse or an RNAse to allow removal of non-desired DNA or RNA components prior to step a).

16. The method of claim 1, wherein the nucleic acids are DNA.

17. The method of claim 1, wherein the nucleic acids are RNA.

18. The method of claim 1, wherein the nucleic acids are selected from the group consisting of: plasmid, genomic, mitochondrial, vesicle, and cell free sources.

19. The method of claim 1, wherein the nucleic acids bind to the silica nanomembranes.

* * * * *